United States Patent [19]
Neward

[11] 3,989,038
[45] Nov. 2, 1976

[54] FETAL ELECTRODE AND BIOPSY DEVICE

[76] Inventor: Theodore C. Neward, 521 Scripps Drive, Claremont, Calif. 91711

[22] Filed: Dec. 15, 1975

[21] Appl. No.: 641,033

Related U.S. Application Data

[63] Continuation-in-part of Ser. No. 526,526, Nov. 25, 1974, abandoned.

[52] U.S. Cl. ............................ 128/2 B; 128/2.06 E; 128/418; 128/DIG. 4
[51] Int. Cl.² ...................... A61B 10/00; A61B 5/04
[58] Field of Search .......... 128/2 B, 2.06 E, DIG. 4, 128/418, 361

[56] References Cited
UNITED STATES PATENTS

| | | | |
|---|---|---|---|
| 3,120,227 | 2/1964 | Hunter, Jr. et al. | 128/418 X |
| 3,326,207 | 6/1967 | Egan | 128/2.06 E |
| 3,421,511 | 1/1969 | Schwartz et al. | 128/418 |
| 3,580,242 | 5/1971 | La Croix | 128/2.06 E |
| 3,628,522 | 12/1971 | Kato | 128/2 B |
| 3,750,650 | 8/1973 | Ruttgers | 128/2.06 E |
| 3,800,784 | 4/1974 | Kiszel et al. | 128/2.06 E |
| 3,804,080 | 4/1974 | Ruttgers et al. | 128/2.06 E |
| 3,827,428 | 8/1974 | Hon et al. | 128/2.06 E |

FOREIGN PATENTS OR APPLICATIONS

| | | | |
|---|---|---|---|
| 146,433 | 8/1962 | U.S.S.R. | 128/2 B |

OTHER PUBLICATIONS

Deutsch Gesundheitsw, 26:pp. 1756–1758, 9 Sept. 1971.

Primary Examiner—Kyle L. Howell
Attorney, Agent, or Firm—Lyon & Lyon

[57] ABSTRACT

There is disclosed herein a medical instrument in the form of an elongated member having at its distal end a plug structure with a removable section and having at its proximal end a manually operable device for causing a predetermined motion of the removable section. The medical instrument is used by insertion of the distal end into a body cavity for performing a medical procedure. In a preferred form, the medical instrument comprises an electrode assembly wherein the plug structure at the distal end includes one or more electrodes useful, for example, in monitoring fetal heartbeat. In an alternative form, the plug structure at the distal end includes a surgical tool for removing tissue for enabling a biopsy to be performed. In either instance, the plug structure at the distal end includes a stationary member and a movable support for causing either an electrode, or the surgical tool, to pivotally move away from and toward the stationary member for engaging tissue. The manually operable device at the proximal end may include a ratchet and cam assembly which operates through a wire or other elongated connector member to cause pivotal movement of the movable support member.

26 Claims, 11 Drawing Figures

FETAL ELECTRODE AND BIOPSY DEVICE

This application is a continuation-in-part of a copending application filed Nov. 25, 1974; Ser. No. 526,526, entitled MEDICAL INSTRUMENT now abandoned.

BACKGROUND OF THE INVENTION

The present invention relates to a medical instrument which may be structured in either of two similar forms to provide an electrode or a surgical cutting tool. In a preferred form of the invention, the same comprises an improved bipolar electrode structure adapted to be inserted through the vagina and cervix of a woman in labor and into contact with the fetus. The distal end of the device includes an electrode structure having two electrodes, a first of which is arranged to engage the tissue or skin of the fetus by remote manipulation of such first electrode. The two electrodes may be connected through suitable wires to an amplifier and a cardiotachometer for recording the fetal electrocardiogram and heart rate during labor and delivery.

In a second structural form, a surgical tool is substituted for the first electrode and can be similarly remotely manipulated for removing a piece of tissue from within a cavity of the body for purposes of performing a biopsy thereon.

While not intending to be limited thereby, the invention and background thereof will be described with respect to the preferred bipolar electrode structure form.

Various forms of electrodes for monitoring purposes have been devised. The structures typically include one or more electrodes, electrical conductors connected therewith, and means for facilitating insertion of the electrode or electrodes within the body. Notable examples of such devices are found in Hunter et al U.S. Pat. No. 3,120,227, La Croix U.S. Pat. No. 3,580,242, Ruttgers U.S. Pat. No. 3,750,650 and Hon et al U.S. Pat. No. 3,827,428. One of the problems associated with attempts to monitor fetal heartbeat and the like is that of properly attaching the electrode to the fetus. In a bipolar electrode structure, two electrodes are used, one of which is attached to the fetus, and the other of which usually is disposed in the vaginal fluid and serves as a reference electrode. The two electrodes typically are of predetermined surface area and sometimes have a predetermined spacing between the two. While the second electrode generally presents no problem from the standpoint of the placement thereof, the first electrode does. The aforementioned Hunter patent shows an electrode in the form of a "C", the ends of which may be closed to engage the tissue by moving a plastic sleeve over the electrode. The La Croix patent discloses an arrangement wherein the first electrode has a fish-hook configuration. The Ruttgers patent discloses an electrode structure wherein the first electrode is in the form of a double helix which is screwed into the tissue. The Hon et al patent discloses an electrode structure wherein the first electrode may be in the form of a point and an auxiliary sharpened helix facilitates attachment thereof to the tissue, and discloses an electrode structure wherein the first electrode is in the form of a single helix which can be screwed into the tissue. The Hon et al patent discloses an electrode structure which is an improvement over certain prior electrodes in that ready insertion of the electrode structure and attachment of the first electrode to the fetus is possible.

The bipolar electrode structure in operation provides a path for current, from the monitored fetus to the recording equipment, with a magnitude very small, such as only milliamps. Noise interference problems have been substantially overcome by making a bipolar electrode structure through injection molding techniques. An example of such techniques and an electrode manufactured thereby is described in applicant's copending application Ser. No. 366,701, filed June 4, 1973, entitled "A Method of Making A Bipolar Electrode Structure", now U.S. Pat. No. 3,890,420. A prior are difficulty of making suitable bipolar electrode structure was the criticality of the exposed surface area ratio between the first electrode and the second electrode. It has been determined that the exposed surface area of the second electrode preferably is twice that of the exposed surface area of the first electrode. If this surface area ratio is substantially varied, the signal-to-noise ratio of the system becomes a significant inhibiting factor in the monitoring operation. This difficulty has been substantially overcome in accordance with the molding techniques and structure described in said copending application.

Although improvements have been made in preventing the helical type first electrode from piercing the fetal epidermis too far because of the electrode structure and manual driving arrangement therefore, it has been found that it still is possible in some instances to screw the helix type electrode too far into the fetus, possibly resulting in tearing or removal of fetal tissue.

On the other hand, in the preferred form of the present invention, the electrode structure includes a first electrode which is pointed and which may be remotely controlled to pivot with respect to a stationary block. With this arrangement, the distal end of the structure containing the stationary member and pointed first electrode is essentially "closed" during insertion into the body, and then may be "opened" by remote activation, to be described below, to cause the first electrode to engage the fetal epidermis but without allowing excessive penetration.

In a preferred form of the present invention, the same includes an elongated and curved guide tube. A plug structure is disposed at the distal end and comprises the electrode assembly having the stationary member and the pointed and pivotal first electrode. The electrode assembly also includes the second or reference electrode, and this entire assembly is encapsulated in plastic to form a unitary plug structure. This electrode structure is disposed in the distal end of the guide tube, and wires from the two electrodes extend through the guide tube to the proximal end of the guide tube. The doctor inserts the distal or forward end of the curved guide tube, including the electrode assembly, through the vagina of the mother and cervix until the first electrode and the block assembly make contact with the fetal head or other portion of the fetus.

A ratchet and cam assembly is disposed on the proximal end of the guide tube and engages the wire connected to the first electrode. By moving a lever, this wire essentially is "pulled" to cause the first electrode to pivot away from the stationary member of the electrode assembly. Once the fetus is contacted, the lever can be moved to allow the first electrode to pivot or spring back to its normal position to thereby physically engage and couple with the fetus. In this manner the end of the first electrode, which may be pointed, pierces the tissue of the fetal epidermis and makes good electrical and mechanical contact therewith. Once the electrode structure is attached to the fetus, the guide tube and the ratchet and cam assembly on the proximal end thereof are removed from the mother, thereby leaving only the bipolar electrode assembly and the wires connected therewith. The entire apparatus is disposable after use.

In the alternative form of the invention as mentioned earlier, the second electrode is not necessary, and the first electrode is replaced by a surgical cutting tool. A wire, cable or other suitable flexible connecting means is connected between the support for the surgical tool and the ratchet and cam arrangement. This enables the surgical tool to be moved away from the stationary member by movement of the lever of the ratchet and cam arrangement, and to return toward the stationary member for engaging, cutting and removing a piece of tissue for biopsy purposes.

SUMMARY OF THE INVENTION

It is the principal object of the present invention to provide an improved electrode.

Another object of the present invention is to provide an electrode structure of improved form including a remotely pivotable electrode and means for operating the same.

Another object of the present invention is to provide an improved surgical tool including a remotely pivotable cutting member.

Another object of the present invention is to provide a simple ratchet and cam mechanism.

DETAILED DESCRIPTION OF PREFERRED EMBODIMENTS

Figures 1, 3A, 3B:
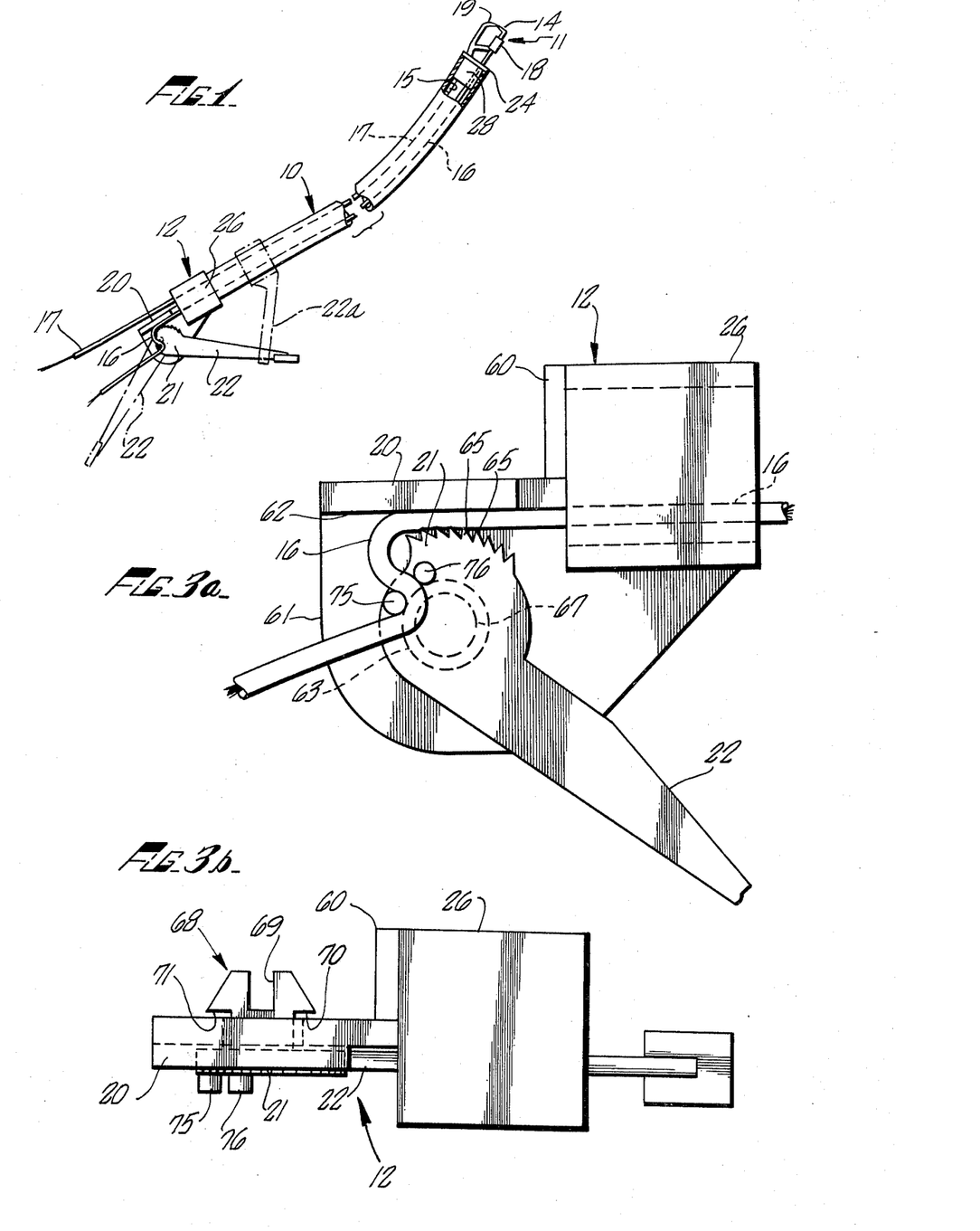
FIG. 1 illustrates an embodiment of the surgical instrument according to the present invention which includes a bipolar electrode assembly useful in obtaining a fetal electrocardiogram and heart rate during labor and delivery.
FIG. 3a is a side view of a ratchet and cam arrangement of the instrument of FIG. 1.
FIG. 3b is an end view thereof.
Figures 2A, 2B, 2C, 2D:
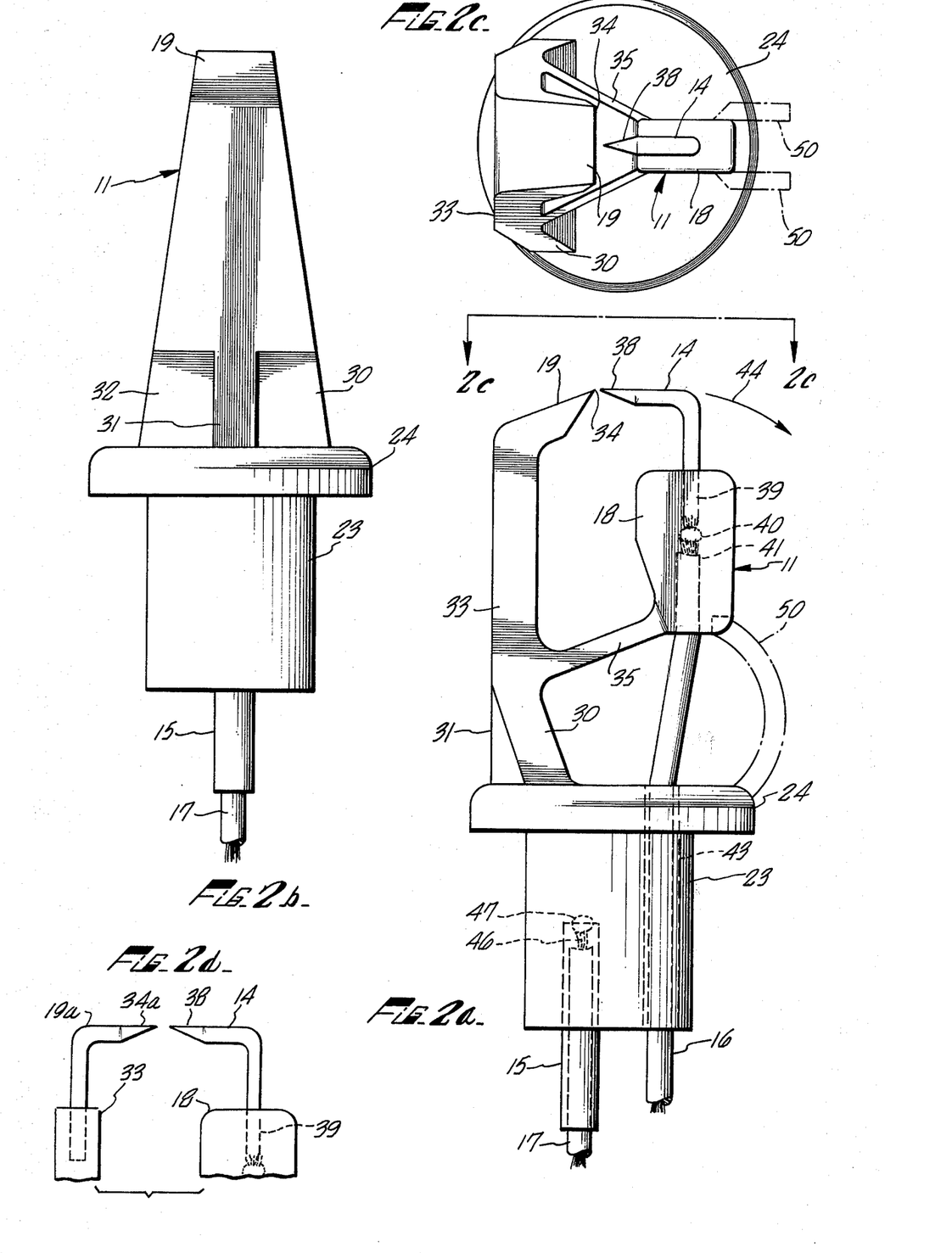
FIG. 2a is a front elevational view of an electrode assembly which may be included in the instrument of FIG. 1.
FIG. 2b is a side view of the electrode assembly rotated ninety degrees.
FIG. 2c is a partial top view.
FIG 2d is an alternative form.

Turning now to FIG. 1, a preferred form of the medical instrument of the present invention is shown and includes an elongated, curved and hollow guide tube 10, an electrode assembly 11 at the forward or distal end thereof, and a ratchet and cam mechanism 12 at the proximal end thereof. Further details of the electrode assembly 11 are shown in FIGS. 2a, 2b and 2c, further details of the ratchet and cam arrangement are shown in FIGS. 3a and 3b.

Before describing these components in detail, it should be noted that the electrode assembly 11 is a bipolar electrode having a first distal metal electrode 14 and a second reference electrode 15. Insulated electrical wires 16 and 17 respectively extend from these electrodes through the inside of the guide tube 10 and extend outwardly from the proximal end thereof. The proximal ends of these wires are adapted to be coupled to suitable electronic equipment such as an amplifier and a cardiotachometer for recording the fetal electrocardiogram and heart rate of a fetus during labor and delivery. The distal end of the wire 16 which is electrically connected to the first electrode 14, also is physically coupled with a movable electrode support 18. By pulling the wire 16, the support 18 pivots and causes the first electrode 14 to pivot away from a stationary member or block 19.

The proximal end of the wire 16 connected to the first electrode 14 extends between the stationary wire block 20 and a cam 21 of the ratchet and cam assembly 12, whereby movement of a lever 22 coupled with the cam 21 causes the wire 16 to be pulled or released.

The electrode assembly 11 is in the form of a plug structure having a plug 23 and cap 24. The plug 23 extends into the distal end of the guide tube 10, but is a loose fit and readily removable therefrom to allow the guide tube 10 to be withdrawn from the body after the electrode 14 is coupled with the fetus. The ratchet and cam assembly 12 includes a cap 26 which is a pressfit on the proximal end of the guide tube 10 because it normally is not necessary to remove the assembly 12 from the guide tube 10.

After the electrode 14 is coupled with the fetus, the lever 22 of the ratchet and cam assembly 12 is rotated as noted above to allow the wire 16 to be disengaged. After this is done, the guide tube 10 and assembly 12 are removed from the body thereby leaving the electrode 14 attached to the fetus. The wires 16 and 17 then can be connected to suitable monitoring equipment. The entire assembly of the tube 10, electrode assembly 11 and mechanism 12 are disposable after use. A lever harness, shown in dotted lines 22a, may be used to retain the lever 22 in a predetermined position during shipment.

In use the electrode assembly 11 and the end of the guide tube 10 are inserted through the vagina and cervix of a woman in labor, and the electrode assembly 11 is moved into contact with the fetus. The lever 22 of the assembly 12 then is rotated (counterclockwise as seen in FIG. 1) to cause the wire 16 to be pulled (to the left as seen in FIG. 1) thereby pivoting the end of the first electrode 14 away from the end of the stationary block 19 of the electrode assembly 11. When the fetus is contacted, the lever 22 of the assembly 12 can be rotated (clockwise as seen in FIG. 1) to disengage the wire 16 and allow the first electrode 14 to pivot back toward the stationary block 19 to its normal position (as shown in FIG. 1). This action allows the first electrode 14 to pierce the fetal epidermis and essentially "pinch" the same between the end of the first electrode 14 and the end of its stationary block 19, thereby providing good electrical and mechanical contact. As will be explained subsequently, the electrode assembly 11 includes a web forming a spring to allow this pivoting action of the first electrode 14 to occur.

Turning now to the details of the electrode assembly 11, the same are more fully shown in FIGS. 2a and 2b. As previously noted, the electrode assembly 11 includes a first electrode 14, second electrode 15, and a stationary block 19. The block 19 preferably is pointed as seen in FIG. 2a. The assembly 11 also includes a plug 23 and a cap 24. As will be apparent, the plug 23 is cylindrical and fits into the distal end of the guide tube 10. The fit thereof is secure, but sufficiently loose to allow the guide tube 10 to be separated from the plug 23 once the first electrode 14 is attached to the fetus. Ribs 30 through 32 extend upwardly from the upper surface of the cap 24, forming at their upper ends a block support section 33, ultimately terminating in the stationary block 19 which has a pointed end 34 facing the end of the first electrode 14. Extending angularly out from the rib 30–32 section and support 33 section is a spring web 35 which terminates in a movable electrode support 18. As will be explained subsequently, the electrode assembly 11 can be injection molded.

The outer end 38 of the first electrode 14 may be pointed as shown in FIG. 2a, and the lower end 39 thereof is soldered at 40 to the electrical conductors 41 of the wire 16. The upper end of the wire 16 (as well as the lower end 39 of the electrode 14) is encapsulated in the support 18 and thus is physically secured thereto. The wire 16 extends through an opening 43 through the cap 24 and plug 23. With this arrangement, it will be apparent that pulling the wire 16 (downwardly as viewed in FIG. 2a) will cause the first electrode 14 to pivot in a manner as indicated by line 44 in FIG. 2a, and this electrode can be allowed to return in a counterclockwise direction because of the spring action of the web 35.

The second electrode 15 is imbedded in the plug 23, and the electrical conductors 46 of the wire 17 are soldered at 47 to the inner end of the second electrode 15.

The first electrode 14 may be of stainless steel, silver, silver-silver chloride, or other suitable metal which will enable sufficient electrical contact to be made with the fetus. The second electrode 15 may be made of a like or similar material. The exposed area of the second electrode 15 preferably is twice that of the exposed surface area of the first electrode 14. The end 38 of the first electrode 14 may be sharp or pointed to facilitate better attachment and contact with the fetus. An exemplary first electrode 14 may be formed of twenty thousandths inch diameter solid stainless steel wire, and the second electrode 15 may be formed from a piece of stainless steel tubing having an inside diameter of approximately fifty thousandths inch, a one-sixteenth inch outside diameter, and with a one-eighth inch-length exposed.

Except for the first and second electrodes 14 and 15 and their respective connecting wires 16 and 17 and solder, the entire electrode assembly 11 preferably is plastic. These components preferably are injection molded with a suitable plastic material to form a unitary electrode structure 11. An exemplary material is nylon because of its good resilience, particularly for the spring web 35, although other materials such as a rigid polyethelene, polypropylene or an acetal resin, or other suitable plastic materials, can be used. The spring web 35 can be molded of any desired thickness and cross-section, but typically, the same will be of a rectangular or cylindrical cross-section. The spring action of the web 35 can be changed by the wall thickness thereof or other materials can be used to provide the desired resilience and result of achieving proper tension to create good electrical contact and to hold the first electrode 14 onto the skin of the fetus. If added resilience is desired, a piece of metal, such as a short piece of spring metal, may be embedded in the electrode assembly 11 within the spring web 35. Additionally, a second loop or web shown in dashed lines 50 also can be molded between the support 18 and the cap 24 to provide more spring tension as desired. Typically, the included angle between the web 35 and the block section 33 is approximately seventy degrees (although the same can be changed or varied) to thereby provide a wide arc (as indicated by line 44 in FIG. 2a) as the first electrode 14 is moved away from and toward the stationary block 19. The stationary block 19 and the end 34 thereof can be varied in configuration, that is wider or thinner and the like. Alternatively, the stationary block as member 19 may comprise a wire embedded in section 33 as shown in FIG. 2d. The member 19a may be the same in shape and configuration as the electrode 14, such as a solid pointed (34a) and sharp stainless steel wire.

As will be apparent from the foregoing description of FIGS. 1 and 2, pulling of the wire 16 causes the movable support 18 to move pivotally in a clockwise direction as seen in FIG. 2a. The spring web 35 provides resilience to cause the support 18 and the first electrode 14 to return toward a normal position as shown in FIG. 2a with the end 38 of the electrode 14 positioned close to or in contact with the end 34 of the stationary block 19 or 19a.

In the alternative form of the present invention, the second electrode 15 and its respective wire 17 can be omitted, and the first electrode 14 can be in the form of a surgical cutting tool, preferably with an elongated cutting edge 38 to mate with end 34 of block 19, replaced with any suitable flexible connector to cause the support 18 to pivot as noted earlier. With this arrangement, preferably the outer end 38 of the device 14 is elongated and sharpened and arranged to normally engage the end 34 of the stationary block 21. With this structure the support 18 can be pivoted to cause the end 38 of the tool to move away from the end 34 of the stationary block 19 when the flexible connector 16 is pulled. When the connector 16 is released, the end 38 moves toward the end 34 of the block 19 to allow a piece of tissue from inside a body cavity to be severed and removed.

Turning now to the ratchet and cam assembly, the same is shown in greater detail in FIGS. 3a and 3b. This assembly includes the cap 26 which preferably is a force-fit on the proximal end of the guide tube 10. A stop and partial cover member 60 covers a portion of the outer end of the cap 26 and provides additional support for a bracket 61. The wire block 20 extends upwardly from the bracket 61 and has a surface 62 for engaging the outer surface of the wire 16. The bracket 61 also includes a cylindrical aperture 63 for receiving a shaft of the cam 21 and lever 22 assembly. The cam includes a plurality of teeth 65 which can engage the outer surface of the wire 16 and wedge the same between the teeth 65 and the surface 62 of the wire block 20 upon rotation of the cam 21. The gap between the teeth 65 of the cam 21 and the surface 62 of the wire block 20 depends on the external size of the wire 16. The lever 22 extends outwardly from the cam. This assembly also includes a shaft 67 which extends through the aperture 63 in the bracket 61 to allow the rotation of the cam 21 and lever 22 with respect to the bracket 61. The outer end of the shaft 67 may be in the form of split cap 68 having a slot 69 and flanges 70 and 71 (note FIG. 3b) to enable the axle 67 to be pushed into the aperture 63 during assembly and be a snap fit with the bracket 61. Alternatively, a separate cap (not shown) can be secured (as with an adhesive) to the outer end of the shaft 67 for holding the cam 21 rotatably to the bracket 61, while still allowing relative rotation between the two. The cap 26, stop and cover member 60, bracket 61 and wire block 20 may be injection molded as a unitary assembly. Similarly, the cam 21, lever 22, shaft 67, and cap 68 may be molded as one piece. With the arrangement shown in FIGS. 3a and 3b, the wire 16 can be moved approximately one-fourth inch, which is more than ample travel for causing suitable pivotal movement of the movable electrode support 18. Preferably, a pair of gripper pins 75 and 76 are molded into the cam 21 and lever 22 assembly as seen in FIGS. 3a and 3b to hold the end of wire 16 in a kinked position. This arrangement prevents the teeth or serrations 65 from peeling the insulation off the wire 16. Instead of raised pins 75 and 76 as shown, a slot for performing a similar function can be provided in the outer face of the cam 21 to receive the end of the wire 16.

It should be noted that in use the electrode can be opened before insertion or after insertion into the body, and when released the wire 16 loosens as noted earlier and the first electrode 14 engages the fetus. The electrode assembly 11 and ratchet and cam assembly 12 can be molded according to the teachings of said copending application. The entire assembly can be a disposable device and can be manufactured inexpensively.

Referring to FIGS. 4 through 7, a further embodiment of the surgical instrument is illustrated in which similar reference numerals are used for elements which correspond to the first embodiment.

Figures 4, 5, 6, 7:
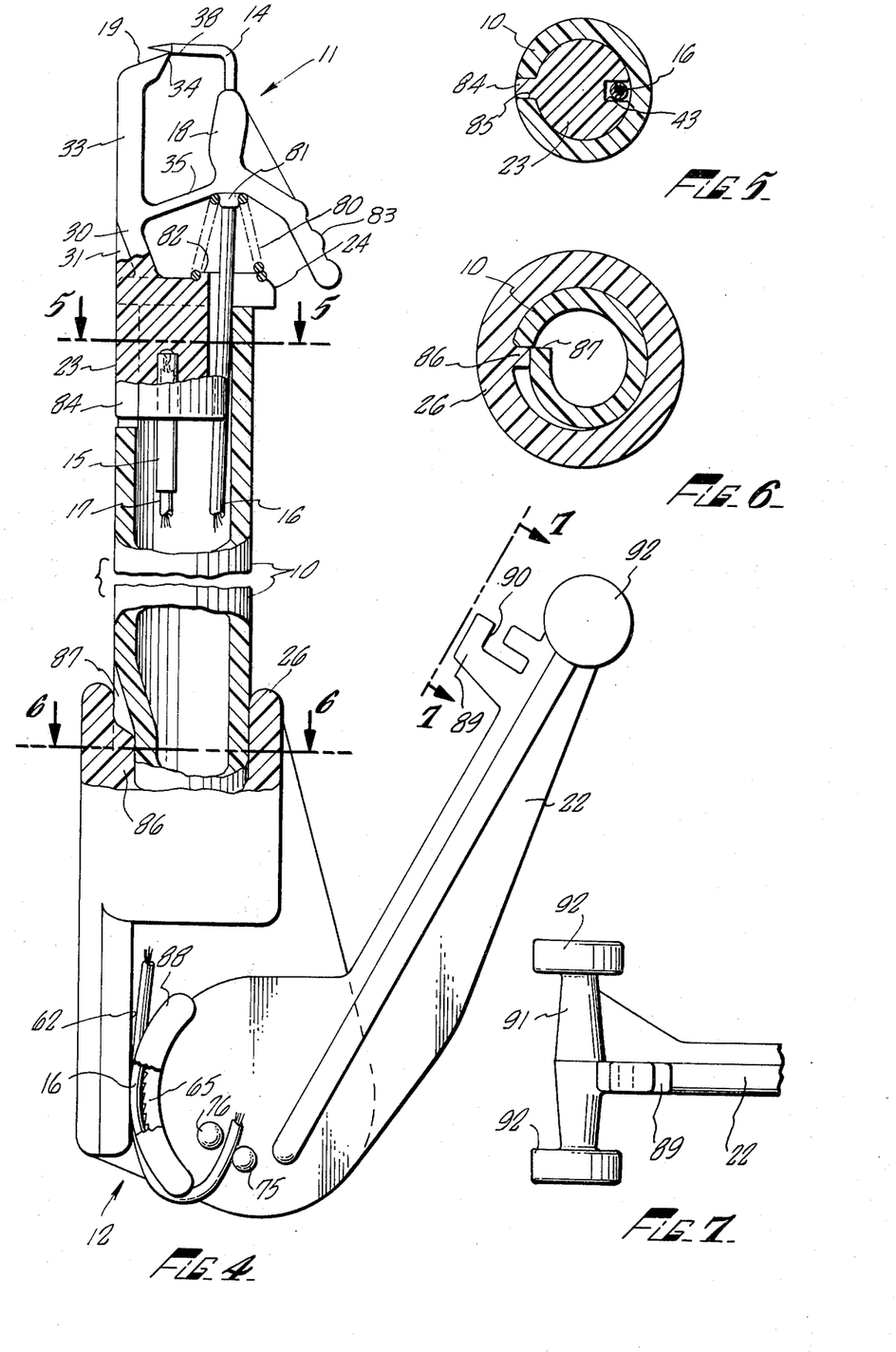
FIG. 4 is an enlarged fragmentary side view of a further embodiment of a surgical instrument, with portions shown in section.
FIGS. 5 and 6 are transverse sectional views thereof taken through 5—5 and 6—6 of FIG. 4.
FIG. 7 is a fragmentary side view thereof taken from 7—7 of FIG. 4.

This embodiment utilizes a tapered coil spring 80, preferably of stainless steel, which is disposed between the cap 24 and support 18 and is retained in place by opposed bosses 81 and 82. The spring supplements a thinner spring web 35. Also the support is provided with an extension forming a small handle 83 whereby after exposure of the head of the fetus, the cap 24 and handle may be gripped between thumb and forefinger to extract the end 38 of the electrode 14 from the scalp of the fetus.

In order to prevent relative rotation of the guide tube 10 and electrode assembly 11, the plug 23 is provided with an external rib 84, and the corresponding end of the guide tube 10 is provided with a slot 85, as shown in FIG. 5.

The cap 26, forming a part of the ratchet and cam mechanism 12, is provided with an internal rib 86, and the corresponding end of the tube 10 is provided with a slit 87, one margin of which is pressed inward to receive the rib as shown in FIG. 6. The rib 84 and slot 85 together with the rib 86 and slit 87 orient the angular position of the ratchet and cam mechanism with respect to the electrode 14. The cam 21 is provided with a semicircular guard flange 88 to aid in retaining the wire 16 in position for engagement by the teeth 65. For use in addition to or in place of the gripper pins 75 and 76, the lever 22 is provided near its extremity with a lateral extension 89 having a gripper slot 90. In order to facilitate manual engagement with the lever 22, its extremity is provided with a cross bar 91 having small head portions 92, as shown in FIG. 7.

The embodiment shown in FIGS. 4 through 7 involves several features which have been found important, particularly in monitoring fetal heartbeat. For example, the spring 80 further insures proper penetration of the end of the electrode 14 into the fetal skin. In addition, as soon as the electrode assembly is exposed, it is desirable to disconnect it from the fetus. Furthermore, it should be readily disconnected under extreme conditions of child birth. The fixed element 33 which supports the fixed prong 19 provides a flat surface and the handle 83 provides a rib which, when engaged by the thumb and index finger, are easily pressed toward each other without causing rotation of the electrode assembly 11 so that disengagement occurs quickly. This is of particular importance when it is realized that this is accomplished through a wetted, hence slippery, glove.

Another feature is the provision of restraints against relative rotation of the electrode assembly and ratchet-cam mechanism which improve the manipulatibility of the instrument, yet do not interfer with disconnection of the guide tube 10. Also the arrangement of the ratchet-cam mechanism has resulted in improved manipulation. That is, the guard flange 88 to retain the tension wire in place, the supplementary gripper 90, and the headed cross bar 91 have all contributed to ease of manipulation under difficult conditions of use.

While embodiments and applications of this invention have been shown and described, it will be apparent to those skilled in the art that many more modifications are possible without departing from the inventive concepts herein described.

What is claimed is:

1. A medical instrument comprising
   elongated guide tube means for enabling a distal end of said instrument to be inserted within a body cavity,
   plug means coupled with the distal end of said tube means, said plug means including
      a proximal portion axially and laterally supported by the distal end of said tube means, and
      a distal portion having an elongated section extending from said proximal portion terminating in a stationary outer end, a movable support section, and a resilient web interconnecting said elongated section and said support section, said web being of sufficient resilience to allow said support section to be moved pivotally by the application of manual force thereto and to pivotally return to a predetermined position with respect to said outer end of the elongated section, and a member extending from said movable support section having an outer sharp end normally closely contiguous to said outer end of said elongated section,
   said proximal portion, elongated section, web and movable support section being a unitary plastic structure, and
   manually operable means coupled with the proximal end of said guide tube means, said manually operable means including flexible means coupled with said movable support section for moving the same to cause pivotal movement of said
   movable support section, said manually operable means including rotatable cam means spaced from a block member, and said flexible means comprising a flexible connector extending between said block member and said rotatable cam means to enable movement of said flexible connector upon predetermined rotation of said cam means.

2. An instrument as in claim 1 wherein
said member extending from said support section comprises a pointed electrode,
said proximal portion of said plug means includes an aperture therethrough, and
said flexible means includes an electrical wire electrically connected with a proximal end of said electrode and physically coupled with said movable support section, said wire extending through said aperture in said proximal portion of said plug means and through said tube means and being adapted to be moved by said manually operable means to cause pivotal movement of said movable support section.

3. An instrument as in claim 2 wherein
said proximal portion of said plug means is removably coupled with the distal end of said tube means, and said proximal portion has imbedded therein and extending therefrom a second electrode, and
an electrical conductor is coupled with said second electrode and extends through said tube means to the proximal end of said tube means.

4. An instrument as in claim 1 wherein
said member extending from said support section comprises cutter means with an elongated and sharp outer end normally disposed in close proximity to the outer end of said elongated section, said outer end of the elongated section being elongated and sharp.

5. A medical instrument comprising
elongated guide tube means for enabling a distal end of said instrument to be inserted within a body cavity,
plug means removably coupled with the distal end of said tube means, said plug means including
a proximal portion having an aperture therethrough and being axially and laterally removably supported by the distal end of said tube means, and
a distal portion having an elongated section extending from said proximal portion terminating in a stationary member having an outer end, a movable support section, and a resilient web interconnecting said elongated section and said support section, said web being of sufficient resilience to allow said support section to be moved pivotally by the application of manual force thereto and to pivotally return to a rest position, and an electrode extending from said movable support section having a pointed end normally closely contiguous to said outer end of said stationary member when said support section is in its rest position,
said proximal portion, elongated section and stationary member, web, and movable support section being a unitary plastic structure, and
manually operable means coupled with the proximal end of said tube means for causing pivotal movement of said movable support section, said manually operable means including an electrical wire electrically connected with a proximal end of said electrode and physically coupled with said movable support section, said wire extending through the aperture in said proximal portion of said plug means and through said tube means and being adapted to be moved by said manually operable means to cause pivotal movement of said movable support section, said manually movable means including rotatable cam means spaced from a block member, and said electrical wire extending between said block member and said movable cam means to enable movement of said wire upon predetermined rotation of said cam means.

6. An instrument as in claim 5 wherein
said proximal portion of said plug means has imbedded therein and extending therefrom a second electrode, and
an electrical conductor is coupled with said second electrode and extends through said tube means to the proximal end of said tube means.

7. A medical instrument comprising
elongated tube means for enabling a distal end of said instrument to be inserted within a body cavity,
plug means removably coupled with the distal end of said tube means, said plug means including
a proximal portion having an aperture therein and being removably supported by the distal end of said tube means, and
a distal portion having stationary block means, a movable support section, and an electrode extending from said movable support section having an end normally closely contiguous to an end of said stationary block means when said support section is in a rest position,
said plug means further including resilient web means connected with said support section, said web means being of sufficient resilience to allow said support section to be pivotally moved by the application of manual force thereto and to pivotally return to the rest position, and said proximal portion, stationary block means, web means, and movable support section being a unitary plastic structure, and
manually operable means coupled with the proximal end of said tube means for causing pivotal movement of said movable support section, said manually operable means including an electrical wire electrically connected with a proximal end of said electrode and physically coupled with said movable support section, said wire extending through the aperture in said proximal portion of said plug means and through said tube means and being adapted to be moved by said manually operable means to cause pivotal movement of said movable support section, said manually movable means including rotatable cam means spaced from a block member, and said electrical wire extending between said block member and said movable cam means to enable movement of said wire upon predetermined rotation of said cam means.

8. An instrument as in claim 7 wherein
said stationary block means includes an elongated section extending from said proximal portion of said plug means and terminated in a block, and said web means includes a web interconnecting said elongated section and said support section and includes loop means interconnecting said proximal portion of said plug means and said support section,
said proximal portion of said plug means has imbedded therein and extending therefrom a second electrode, and an electrical conductor is coupled with said second electrode and extends through said tube means to the proximal end of said tube means.

9. A medical instrument comprising elongated tube means for enabling a distal end of said instrument to be inserted within a body cavity, plug means removably coupled with the distal end of said tube means, said plug means including a proximal portion having an aperture therein and being axially and laterally removably supported by the distal end of said tube means, and a distal portion having an elongated section extending from said proximal portion and terminating in an inwardly extending edge, a movable support section having an inwardly extending electrode, and a resilient web interconnecting said elongated section and said support section, said web being of sufficient resilience to allow said support section to be moved pivotally by the application of manual force thereto and to pivotally return to a rest position wherein the electrode is closely contiguous to said inwardly extending edge of the elongated section, said proximal portion, elongated section, web and movable support section being a unitary plastic structure, and manually operable means coupled with the proximal end of said tube means, said manually operable means including flexible means, extending through said tube means and the aperture in the proximal portion of the plug means, coupled with said movable support section for moving the same to cause pivotal movement of said movable support section.

10. A medical instrument dimensioned for insertion into a body cavity to enable placing the distal end of the medical instrument in contact with body tissue, the medical instrument comprising guide means dimensioned for insertion into a body cavity, an integral structure including an end fitting carried at the distal end of the guide means, a fixed element having a base end integral with the end fitting and an axially extending radially offset portion, a yieldable element extending radially inwardly from the fixed element, and a support element carried by the yieldable element, a fixed prong extending radially inward from the extremity of the fixed element, a movable element having an axially extending radially offset portion imbedded in the support element and a radially inwardly extending movable prong, the support element being biased by the yieldable element to urge the movable prong toward engagement with the fixed prong, the prongs limiting insertion of the guide means upon contacting body tissue, and a tension member attached to the support element and extending outward through the guide means, the tension member adapted, when pulled while the prongs are maintained in contact with the tissue, to move the support element and movable prong away from the fixed prong and permit body tissue to protrude between the prongs, whereby, upon subsequent release of the tension member the protruding tissue is retained between the prongs.

11. A medical instrument as in claim 10 wherein at least one of the prongs is an electrode for piercing the tissue to make electrical contact therewith.

12. A medical instrument as in claim 10 wherein the movable prong is an electrode for piercing the tissue to make electrical contact therewith, a second electrode protrudes from the end fitting of the integral structure, a pair of electrical conductors are connected to the respective electrodes, the conductor connected to the movable prong electrode forming the tension member, and the guide means being removably connected to the end fitting of the integral structure for removal therefrom.

13. A medical instrument as in claim 10 wherein both of the prongs are cooperative cutting elements for severing and retaining a portion of the protruding tissue therebetween for subsequent removal.

14. A medical instrument as in claim 10 which further comprises a lever pivotally mounted at the proximal end of the guide means and engagable manually by one hand, and means on the lever for removable attachment to the tension member for applying tension thereto to effect separation of the prongs.

15. A medical instrument as in claim 10, wherein the movable prong support element is provided with a manually engageable extension movable in a direction to separate the prongs for removal from the tissue therebetween.

16. A medical instrument as in claim 10, wherein a spring element surrounds the tension member and extends between the movable prong support element and the end fitting.

17. A medical instrument dimensioned for insertion into a body cavity to enable placing the distal end of the instrument in contact with body tissue, the medical instrument comprising a guide tube dimensioned for insertion into a body cavity, a distal fitting carried at the distal end of the guide tube, a radially offset fixed element extending axially from the fitting and terminating in a radially inwardly directed fixed prong, a movable prong, a yieldable means for supporting the movable prong in confronting relation to the fixed prong, the yieldable means biasing the movable prong into cooperative relation with the fixed prong, a tension member connected with the movable prong and extending axially through the guide tube, the tension member, when pulled, applying a force to the movable prong in opposition to the yieldable means to separate the movable prong from the fixed prong whereby, upon subsequent release of the tension member, body tissue protruding between the prongs is retained therebetween, a proximal fitting carried at the proximal end of the guide tube, a lever carried by the proximal fitting and extending in angular relation with the adjacent portion of the guide tube, and means for engaging the tension member including a fixed element carried by the proximal fitting, a serrated element and retainer pins carried by the lever arranged to exert tension on the tension member by manually pressing the lever toward the adjacent portion of the guide tube.

18. A medical instrument as in claim 17 wherein
the movable prong is an electrode for penetrating the tissue to make electrical contact therewith, and
the tension member is an electrical conductor for the movable prong electrode.

19. A medical instrument as in claim 17 for connection to sensing apparatus wherein
the movable prong is an electrode for penetrating the tissue to make electrical connection therewith,
a second electrode protrudes from the distal fitting,
a pair of electrical conductors are connected to the respective electrodes, the conductor connected to the movable prong electrode also forming the tension member, and
the guide tube is removable from the distal fitting, and the lever is separable from the conductor tension member, for removal of the guide tube and lever while the electrodes remain attached to the tissue, and the proximal ends of the conductors being available for attachment to sensing apparatus.

20. A medical instrument as in claim 17 wherein
both of the prongs are cooperative cutting elements for severing and retaining a portion of the protruding tissue therebetween for subsequent removal.

21. A medical instrument as in claim 17, wherein the distal and proximal fittings are secured against rotation relative to the guide tube thereby to maintain the fittings in fixed oriented relation.

22. A medical instrument as in claim 17, wherein the means for engaging the tension member further includes a guard for retaining the tension member in position for engagement by the serrated element.

23. A medical instrument as in claim 17, wherein the means for engaging the tension member further includes means forming a gripping slot spaced from the retainer pins.

24. A medical instrument as in claim 17, wherein the lever terminates in a cross member to facilitate manual engagement.

25. A medical instrument dimensioned for insertion into a body cavity to enable placing the distal end of the medical instrument in contact with body tissue, said medical instrument comprising
an integral structure dimensioned for insertion into a body cavity and including a mounting element, a fixed element having a base end integral with the mounting element and an axially extending radially offset portion, a yieldable element extending radially inwardly from the fixed element, and a support element carried by the yieldable element,
a fixed prong radially inward from the extremity of the fixed element,
a movable electrode element having an axially extending radially offset portion imbedded in the support element and a radially inwardly extending electrode prong, the support element being biased by the yieldable element to urge the electrode prong toward engagement with the fixed prong, the prongs limiting insertion of the medical instrument upon contacting body tissue, and
a combination electrical conductor and tension member attached to the support element for accessibility externally of the body cavity, the tension member adapted when pulled to move the support element and movable electrode prong away from the fixed prong and permit body tissue to protrude between the prongs, whereby upon subsequent release of the tension member the protruding tissue is retained between the prongs in electrical contact with the electrode prong.

26. A medical instrument as in claim 25 wherein
a second electrode protrudes from the mounting element for electrical contact with fluid present in the body cavity, and
a second electrical conductor element for accessibility externally of the body cavity extends from the second electrode.

* * * * *